United States Patent [19]

Amano et al.

[11] 4,138,638
[45] Feb. 6, 1979

[54] APPARATUS FOR EXAMINING LIQUID QUALITY

[75] Inventors: Kenichi Amano; Noboru Furuya, both of Tokyo, Japan

[73] Assignee: Kabushiki Kaisha Meidensha, Tokyo, Japan

[21] Appl. No.: 839,740

[22] Filed: Oct. 5, 1977

Related U.S. Application Data

[63] Continuation of Ser. No. 609,795, Sep. 2, 1975, abandoned.

[30] Foreign Application Priority Data

| Sep. 6, 1974 [JP] | Japan | 103337 |
| Sep. 9, 1974 [JP] | Japan | 103669 |
| Oct. 31, 1974 [JP] | Japan | 126295 |
| Dec. 24, 1974 [JP] | Japan | 1563 |

[51] Int. Cl.² ........................... G01N 27/42
[52] U.S. Cl. ........................... 324/29; 204/273
[58] Field of Search .............. 204/32, 1, 141, 195 R, 204/273, 277; 324/30 R, 30 B, 29

[56] References Cited

U.S. PATENT DOCUMENTS

| 3,039,951 | 6/1962 | Clenard et al. | 204/273 |
| 3,282,823 | 11/1966 | Richards | 204/273 |
| 3,412,004 | 11/1968 | Winters | 204/273 |
| 3,630,860 | 12/1971 | Fox | 204/273 |
| 3,647,646 | 3/1972 | Tucker et al. | 204/273 |
| 3,959,112 | 5/1976 | Arend | 204/273 |

Primary Examiner—M. Tokar
Attorney, Agent, or Firm—Haseltine, Lake, & Waters

[57] ABSTRACT

An apparatus for examining liquid quality, for example, water quality, in which a sensing element is placed in contact with the test water, and which comprises sensing means including a sensing element, means for generating an air bubble in the vicinity of the sensing element and for producing a turbulent flow due to the substantially disordered motion based on the floating power of the air bubble in the vicinity of a sensing surface of the sensing element.

11 Claims, 19 Drawing Figures

APPARATUS FOR EXAMINING LIQUID QUALITY

This is a continuation of application Ser. No. 609,795 filed Sept. 2, 1975 now abandoned.

BACKGROUND OF THE INVENTION

This invention relates to an apparatus for examining water quality, and more particularly to a water quality determination apparatus in which a sensor element is placed in contact with the water under investigation to electrochemically determine indications of representing the water quality of polluted rivers, lakes, marshes sewage and waste waters.

Of the water quality determination device of the kind described, an electrochemical type sensor element includes dissolved oxygen meters, PH meters, oxidation-reduction potentiometers, and other meters for determining concentrations of various ions by selective ion electrodes. An optical type sensor element includes immersed type turbidity meters and suspended solid concentration meters.

As a water resource has been contaminated, a treating and a monitoring techniques have established by way of preventation of the pollution of water resources. Various kind of measuring devices are used in putting the treating and supervising techniques to practical use. However, a first problem encountered in using these devices is that, as the objections of measurement are polluted rivers, lakes and marshes and sewage and waste waters, the sensing elements as placed in contact with the water to be examined have their own inherent problems such as the lowering of the sensitivity of the electrodes and the inability to measure acculately and continuously as the pollution of a surface of electrode has developed, because the objections of the measurement are sludges and polluted rivers and the like.

Taking the aforementioned dissolved oxygen meter by example, such meter employs an electromechanical reaction. A conventional oxygen meter principally comprises a negative electrode, a positive electrode, an electrolyte and a membrane for protecting these electrodes and the electrolyte from the test liquid. When the sensing element of the dissolved oxygen meter is placed in contact with the test liquid to be examined, gas molecules in the test liquid in the vicinity of the membrane of the sensing surface diffuse into the electrode through the membrane. Namely, the test water in the vicinity of the membrane will become the condition which is lack of the oxygen gas molecules in comparison with the other portions of the test water.

Accordingly, as is the case commonly with all the aforementioned types of dissolved oxygen meter, it is necessary to move the test water at a velocity higher than that of 10 to 50 centimeter per second relative to the sensor element to achieve a high accuracy measurement of the amount of dissolved oxygen by contacting the fresh test water to the membrane. Accordingly, the most significant problem in measuring the amount of dissolved oxygen meter is what may give the velocity of flow to the test liquid.

To work out this problem, when the test liquid is relatively clean, it is possible to give the relative speed between the test liquid and the sensing surface of the sensor which is positioned within a suitable conduit of a conventional mechanical pump.

However, when subjects of measurement are mixed liquid in the aeration tank of the sewage treating station, polluted rivers and lakes, the test liquid to be examined includes an unexpected shape and property matter such as hair, rubber and grindstone or the like, and these matters shorten the life of the mechanical pump. It has been found experimentally that increased effects may be oblained by using an air-lift pump which has a simple construction and has no rotary or frictional portion. Accordingly, as the air-lift pump is simple construction it is only required to remove the obstruction automatically in order to carry out the measurement long interval and continuously.

The second problem encountered in long interval and continuous measuring the dissolved oxygen in the polluted water is that when the dissolved oxygen electrode is immersed in the polluted test water, pollutants such as sludges stick to the surface of the sensing electrode. This means that the change of the effectual thickness of membrane, and especially in case a contamination is an aerobic microorganism which absorbs the effectual change of the thickness of the membrane will become greater and, therefore, the sensitivity of sensing electrode is lowered.

Hithertofore, although an ultrasonic wave, jet water and jet air have been used for the means for removing or preventing the pollutants, there are few cases in which the increased effect can be obtained. Namely, the method using the ultrasonic wave is only effective to remove the contaminate such as sands and sludges which is adhered to the sensor element, and is not effective to remove the cohesive matters consisting of the microorganism adhering to the sensing surface what may be called the sludges. And, further, in the ultrasonic wave cleaning type, there is a disadvantage that is necessary to use a costly ultrasonic wave generating device.

In the method using the jet water to clean the sensing element, as the high pressure water is blow against the sensing surface, it is impossible to clean entirely the sensing surface which is relatively wide surface and is curved shape. The more important disadvantages of the method used the high pressure jet water is the fact that a sensor element having not so mechanical strength is destroyed by the jet water, and costly pressure pump is required. And, furthermore, the more important disadvantages is the fact that the microorganism included in the sludge is destroyed by the jet water. And viewing the jet air means from a standpoint of maintenance free the method of jet water have the following drawbacks that since an air compressor is usually used for obtaining the high pressure air, it is necessary to check an oil, an high pressure tank of the air compressor, and further is required the costly and mechanically strong sensing element.

Refloating and watching a sensing device immersed in the test water during several days, a cohesive matter what may be called a pollutant has been adhered to the sensing surface of the device. A course of adhering and a rate of the cohesive matter is greatly depended upon the water quality and the condition of the flow of the test water. It may, however, be presumed that the pollutant is not chemically connected to components consisting of the sensor element judging from being separated from the sensing surface by wiping up with a piece of cloth or a paper. In fact, a sensitivity of the device recoveres and becomes normal conditions, therefore it may be judged that the pollutant is clinging to the sensing surface only physically. On the other hand, it is found that the adhering speed of the pollutant is reduced as the velocity of flow increases. And the sensitivity recovers to that of clean sensor. These phenomenon has been experimentally confirmed.

SUMMARY OF THE INVENTION

With above in view, it may be presumed that the sensing surface is polluted by the physical adhesion of contaminate floating in the test water, and that the pollutant of the sensing element consists in a laminar sublayer generated in the vicinity of the sensing surface by means of the viscosity of the subject of measurement judging that from the contaminants are removed by the abrupt change of flow velocity and by the decrease of the flow velocity.

It is, therefore, an object of the present invention to provide an economical and maintenance free apparatus for determining the test liquid by removing contaminations attaching to a surface of a sensor element by means of the strong turbulent flow generated by disordered motion due to the floating power of air bubble.

It is another object of the present invention to disclose an apparatus for measuring the quality of a dissolved matter in the polluted liquid and to disclose an apparatus which may prevent the lowering of the sensitivity of a sensor element and the lowering the flow of a test liquid due to the closure of a sampling pump.

Another object of the invention is the provision of an apparatus having a sensor which is enabled to measure at high sensitivity by removing contaminants sticking to a sensor and may enhance the cleaning effect by preventing the clinging of a rough refuse to a cleaning mechanism.

And it is more important object of the present invention to provide an apparatus for determining the water quality as well as for cleaning without destroying a floc.

With above in view, the present invention resides in an apparatus for measuring the dissolved matter in the polluted liquid, which includes an air bubble generating means positioned in the vicinity of a sensing element for obtaining the measuring information, and is characterized that a strong turbulent frow is generated in the vicinity of a sensing element by the substantially disordered motion based on the floating forces of air bubbles by the air bubble generating means.

More specifically, an apparatus according to the present invention includes an air bubble generating means such as an air spray mechanism and an air supplying mechanism for supplying the air to the air spray mechanism. Another modification of the present invention further comprising an air-lift pump which includes a sensing device, a sensing element incorporated in the sensing device and a refuse obstructing member to prevent from clinging rough refuse to the sensing device.

BRIEF DESCRIPTION OF THE DRAWINGS

A better understanding of the present invention may be had from the following detailed description when read in conjunction with the accompanying drawings, in which.

DETAILED DESCRIPTION OF PREFERED EMBODIMENTS

Figure 1:
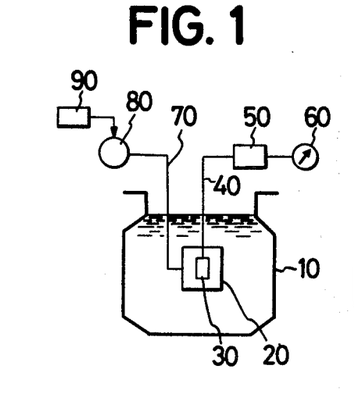
FIGS. 1 and 2 are diagrammatical views illustrating a first embodiment of an apparatus of the present invention.

In FIG. 1, the reference numeral 10 indicates a water source of test liquid for storing the test liquid of polluted rivers, lakes and marshes and sewages; 20 is a sensing device incorporating a sensor 30; the reference numeral 50 is a signal transducer connecting a signal led from the sensor element 30 by way of a signal wire 40; the reference numeral 60 shows an indicating and recording device; the numeral reference 80 is a low pressure supplying source which sends the air through an air conduit 70; and 90 is a timer which drives the air source 80 at the cleaning time to clean the sensing element 30.

Figure 2:
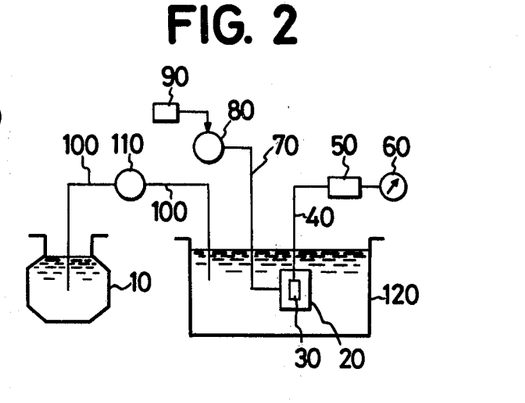

FIG. 2 shows an apparatus for determining the test liquid for measuring the test liquid by immersing the sensing device 30 into the liquid which is stored in another positioned sampling tank 120. And in FIG. 2, numeral 100 is a test liquid pipe; and 110 is a sampling pump.

FIGS. 3 through 6 show various type of sensing device 20 according to a first embodiment of the invention. The sensing device 20 of the first embodiment comprises a sensing means including a casing 26, a sensing element 30 incorporating into the casing, air bubble generating means positioned near the lower portion of the sensing element 30 and air supplying means for supplying the air to the air bubble generating means.

Figure 3:
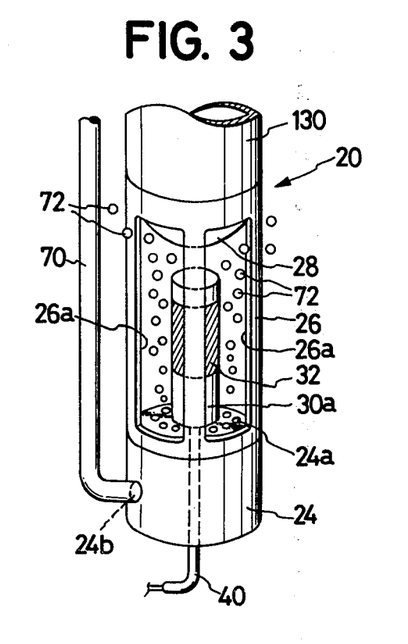
FIGS. 3 to 6 are fragmentary schematic elevational front views of sensing devices which may advantageously be used in conjunction with the apparatus of FIGS. 1 and 2.

FIG. 3 of the drawings shows a sensor assembly employing a side face detecting type dissolved oxygen meter 30a having a sensing surface 32 positioned on the side surface of a cylindrical sensing element 30. A sensing device 20 of FIG. 3 includes an air bubble generating member such as a mainfold type tubular air spraying member 24 having an air inlet opening 24b apertured on the outer side surface, air spraying holes 24a apertured at the upper surface of the air spraying member 24, a side detecting type dissolved oxygen meter 30a disposed on the center portion of the upper surface of the air spraying member 24 and a cylindrical casing 26 connected to a holder 130 for positioning the dissolved oxygen sensing element 30a to the suitable place. The one end of the casing 26 is interconnected to the air spraying member 24, and a plurality of rectangular window 26a is apertured on the circumferential surface of the casing 26 so that the test liquid may flow in and out therethrough. And an air bubble guide member 28 forms a circular cone shape and positioned in a upper end portion of the casing 26. A conduit 70 is connected and communicated to the air inlet opening 24b.

When the sensor 20 is immersed in the test water, a part of the test water flows in and out through the window 26a contacting with the sensing element 30a, and at this time the amount of the dissolved oxygen is detected by the sensing element 30a. The detected signal from the sensing element 30a is presented to the signal transducer 50 by way of the signal wire 40. At the time for cleaning the sensing element 30a, the timer 90 operates and drives the air pump 80. When the air pump 80 is operated, the air is supplied to the air spraying member 24 through the air conduit 70. The air distributed into the air spraying member 24 is ejected out from the spraying holes 24a, and the ejected air from the spraying holes 24a becomes air bubbles 72. The air bubbles 72 generating from the spraying holes 24a is lifted by buoyancy of the test water towards the upper direction of the water with moving the disordered motion around the sensing surface 32 of the sensing element 32a.

In this instance, the air bubbles 72 are smoothly led to the outer by the air bubbles guiding member 28 from the interior of the casing 26 without halting within the casing 26. And the extensive turbulent flows are generated in the vicinity of the sensing surface 32 by means of the air bubbles ejected from the spraying holes 24a, and laminar subflows are separated from the sensing surface 32 of the sensing element 30a, so that the pollutants sticking to the sensing surface 32 is removed therefrom.

In this case, as the air pressure in the air spraying member 24 requires the atmosphere only to be able to generate the air bubbles 72 from the air spraying holes 24a, the low pressure air source may be fully usable for obtaining approximately from 0.5 to 1 atmospheric pressure. Additionally, as the turbulent flow is used for a cleaning means, it is more effective that the air spraying holes 24a should be placed, in the test liquid, more or less spaced apart from the sensing element 30a.

Figure 4:
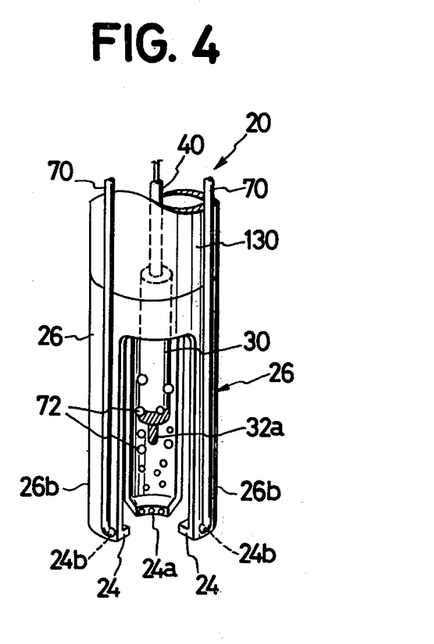

Referring to FIG. 4 of the drawings, shown is another modification of the first embodiment. As is best shown in FIG. 4, a sensing device 20 includes a tubular holder 130, a casing 26 connected to an end portion of the holder 130, a plurality of projections 26b extending from an open end portion of the casing 20 and a cylindrical sensing element 30 incorporated in the casing 26 and between the projections 26b. The cylindrical sensing element 30 is vertically mounted on the center portion of the tubular holder 130, and the projections 26b are provided on the open end portion of the casing 26. Air spraying members 24 are mounted on a pointed end of each projection 26b toward the inner direction of the projection 26b. Air spraying holes 24a is apertured on the inner surfaces of air spraying member 24, and air inlets 24b are apertured on the outer circumferential surface of each projection 26b, and air conduits 70 are connected to the air inlets 24b.

According to the sensing device 20 shown in FIG. 4, the air injected through the conduit 70 into the spraying member 24 changes into the many air bubbles 72, and the air bubbles 72 lift along to the sensing surface 32a from the just under a pointed end of the sensing element 32a to the upper wards of the sensing element 30 so as to move disordered and surrounding the sensing surface 32a. Therefore, the extensive turbulent flow is generated around the sensing surface 32a, and the laminar sub-layer is removed and the sticking matter is detached from the sensing surface 32a.

Figure 5:
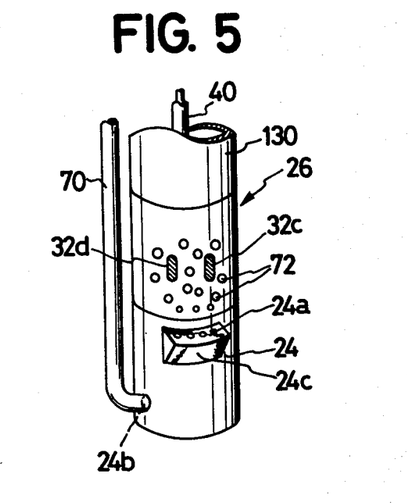
Figure 6:
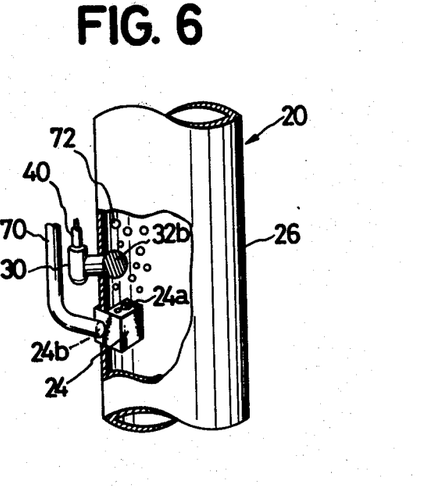

Another forms of the sensing device 20 is best shown in FIGS. 5 and 6. A sensing device 20 illustrated in FIG. 5 is a light diffusion type concentration meter. As is best shown in FIG. 5, a light source 32c and a receiving portion 32d are disposed on a part of a tubular casing 26, and a manifold 24c is fixed to the lower portion of the outer side surface of the spraying member 24.

FIG. 6 shows an ultrasonic wave type concentration density meter, and a sensing surface 32b of a sensing device 20 is disposed in a inner wall surface of casing 26. As is best shown in FIG. 6, the sensing element 30 is secured to the side surface of the casing 26, and at the same time the sensing surface 32b is positioned within the inner surface of the casing 26. A spraying member 24 is fixedly secured to the inner wall surface of the casing 26, and an air conduit 70 is connected an air inlet 24b of the spraying member 24.

As is stated above, according to the apparatus of the first embodiment, the air bubble generating means such as the air spraying member 24 is located to the downward of the sensing element 30, and employed as the washing means is the turbulent flow which is generated and induced by the disordered rising motion of the air bubbles 72. Consequently, it can be seen that, even if the sensing element 30 has not so mechanical strength, the washing of the sensing element 30 can be easily and completely accomplished.

Furthermore, it can also be seen that since the sensing device 20, in general, is not almost immersed into the deep portion of the test liquid, the spray pressure of the air may only be slightly higher than the water pressure of the test water, and a low pressure air source such as a conventional small air pump or a blower may fully be used as an air supplying source. It has been found experiencedly that these air pump and blower are not almost out of ordered and are maintenance free.

Figures 7, 8:
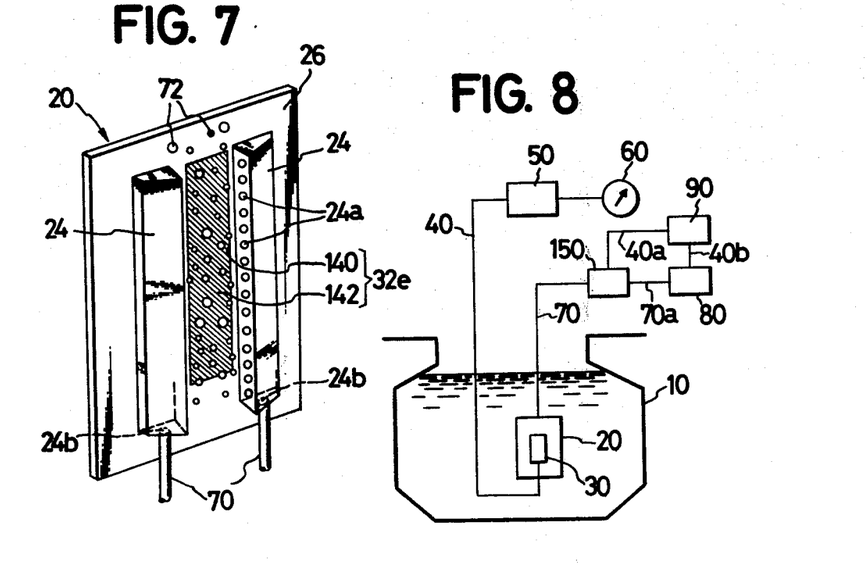
FIG. 7 is a schematic view illustrating another example or second embodiment of an apparatus of the present invention.
FIG. 8 is a block diagram of a third embodiment of the apparatus according to the present invention.

FIG. 7 shows a second embodiment of the invention. As is best shown in FIG. 7, in an apparatus of the second embodiment, an air bubble generating member is placed in the vicinity of the side face of the body to be cleaned, and the air bubbles is blow to the direction of side face of the body to be cleaned. A sensing device 20 of FIG. 7 is used for the optical type sludge settling meter, and a rectangle-shaped opening 140 is opened to the casing 20, a translucent 142 such as a glass is fitted thereto, and an observation window 32e is formed by the translucent 142. A pair of air spraying members 24 are provided and located vertically extending opposedly at the vicinity of both side of the observation window 32e, and air spraying holes 24a, 24a are provided at the opposing surfaces of air spraying members 24, 24.

Air inlets 24b is apertured at the lowermost side face of the air spraying member 24. The air inlet 24b is communicated with the air pipe 70.

Thanks to the sensing device 20 of FIG. 7, as the air bubbles 72 are blown out horizontally against the side face of the observating window 32e, the air bubbles 72 effectively concentrate to the sensing surface that is observing window 32e and rise towards the upper direction by moving disordered motion. The turbulent flow generates effectively near the window 32e, and therefore the cleaning efficiency is enhanced. Additionally, although the above description is made about the sendimentation settling meter in FIG. 7, the second embodiment of the present invention is not limited to the sendimentation settling meter of FIG. 7, and is applicable to, for example, the sensing device 20 shown in FIG.

3. Namely, in the sensing device 20 of FIG. 3, it may possible to produce the air bubbles 72 from the inner circumferential portion of the casing 26 by providing the air spraying member on the inner surface of the casing 26.

Concerning the cleaning of the sensing device, it has been found experimentally that the contamination can be removed from the sensing surface almost 100 percent and completely by means of wrapping the sensing element with the air bubbles floating and rising at the disordered motion. And it has also been found experimentally that when the air bubbles are rising at the portion of spaced-apart portion, the increased effect of cleaning may not be obtained in spite of the turbulent flow.

Accordingly, it is very significant that the air spraying hole must be positioned so that the air-bubbles which is lifted by the floating power of the test liquid contacting with the sending element, for the purpose of obtaining the cleaning effect. Furthermore, a large refuse obstructs a washing function and clings to washing mechanism because the flow exist in the test liquid.

Sensing devices shown in FIG. 8 through 12 may solve the above drawbacks. Namely, FIG. 8 illustrates an apparatus of a third embodiment of the present invention. In FIG. 8, similar members are illustrated by the same numbers as that of FIGS. 1 and 2, and at the preset time a timer 90 operates and makes a solenoid valve 150 and an air pump 80 to on and off states temporarily. And morefurther, in this system, the solenoid valve 150 and the signal wire 40a are omissible, and a similar effect can be obtained by means of directly connecting an air conduit 70 and 70a.

Figure 9:
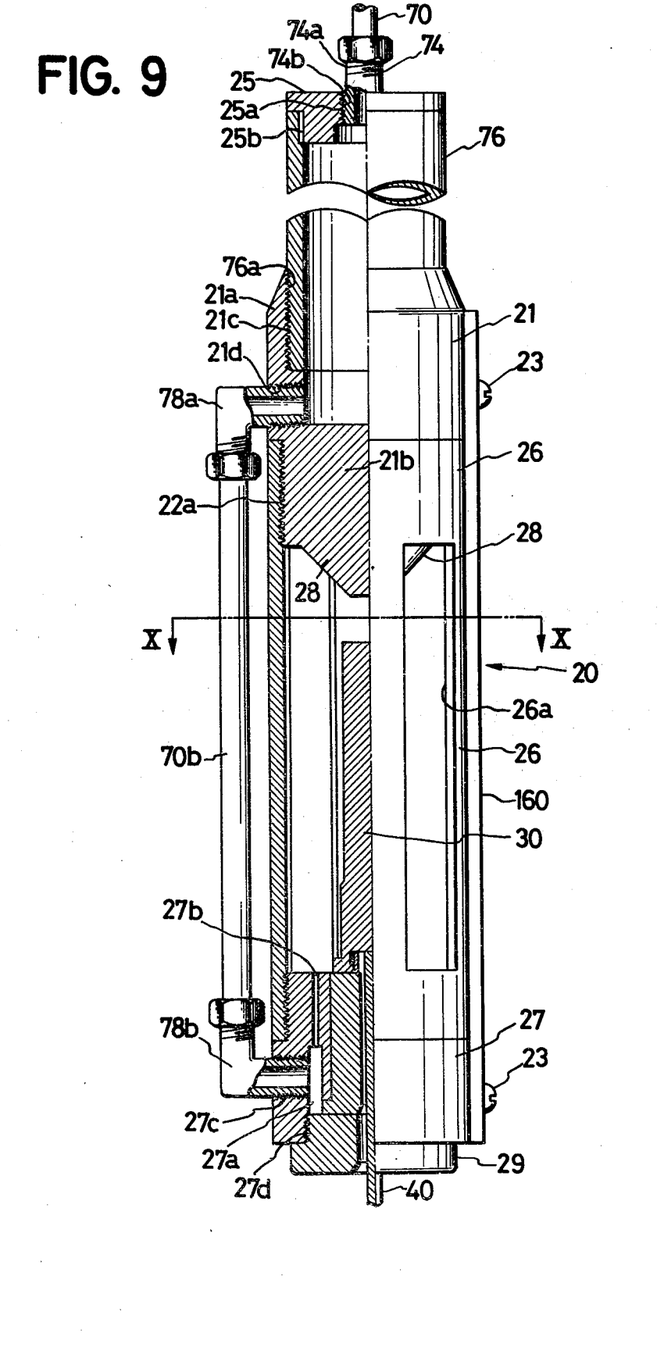
FIG. 9 is a sectional view of a sensing device of the present invention.
Figure 10:
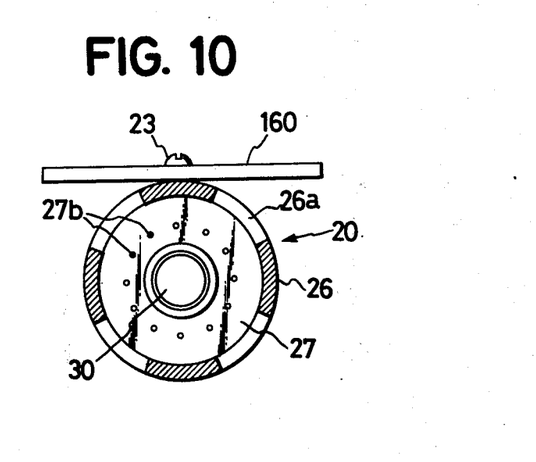
FIG. 10 is partial sectional view taken along line X—X of FIG. 9.
Figure 11:
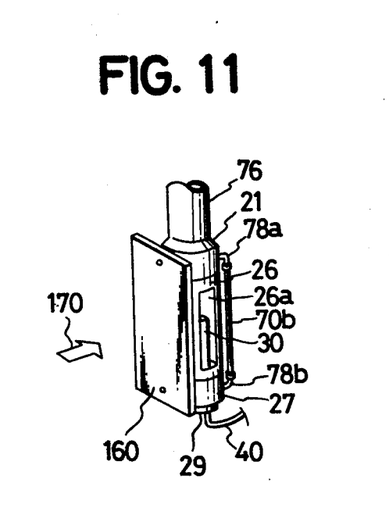
FIG. 11 is a schematic view of sensing device of FIGS. 9 and 10.

The sensing device 20 embodying the invention is best shown in FIGS. 9 and 10, and the sensing device 20 is mainly composed of an upper cap 25 connected to a jointing pipe member 74, a pipe 76 connected to the cap 25, a jointing member 21 secured to the pipe member 76, a casing 26 connected to the jointing member 21 and intercorporating a sensing element 30, an electrode holder 27 securing the sensing element 30 and connected to the casing 26, a lower cap 29 to be fitted and fasten to the electrode holder 27 and a refuse obstructing member 101 fasten to the casing for preventing a rough refuse from clinging to the casing 26.

More specifically, as is shown in FIGS. 9 and 10, the upper cap member 25 is connected to the air conduit 70 through the joint pipe 74, the air conduit 70 is further connected to the solenoid valve 150, and screw portions 74a and 74b are provided on a circumferential surface of the joint pipe 74. A tapped hole 25a is formed at a center portion of the cap member 25. Namely, the air conduit 70 is jointed to the cap 25 in liquid-tight relationship, the cap 25 is jointed to one open end portion of a pipe 76 by the threaded portion 25b. The joint 21 is composed of an hollow cylinder portion 21a, and a circular cone shaped air bubble guiding member 28 and a circular cylinder 21b.

A threaded portion 21c is provided at an inner wall of the hollow cylinder portion 21a of the joint 21. And the joint 21 is threadly connected to an outer circumferential surface of the pipe 76. An L-shaped conduit jointing metal 78a is threadedly connected to a thread portion 21d. Thread portions 22a, 22b are formed at an inner surface of the both open end portions of the tubular casing 26, and the one open end portion of the casing 26 is connected to a thread portion provided on the outer circumferential surface of the circular cylinder 21b. The electrode holder 27 is secured to the other end portion of the casing 26 by a thread portion 22b, and a circular slot 27a is apertured in the electrode holder 27. As is best shown in FIG. 10, holes 27b opened toward the axial direction what may be called the air spraying hole.

And, furthermore, provided on the side surface of the holder 27 is radial tapped hole 27c communicating with the slot 27a, and an L-shaped conduit jointing metal 78b is inserted and connected to the tapped hole 27c, and further the cap 29 is fitted in liquid-tight relationship to the threaded portion 27d formed at the end portion.

The pipe 76 is the pipe for connecting easily to a holder (not shown in FIG. 9), and an upper portion of the pipe 76 is situated for the upper of the test liquid surface on the other hand, the lower portion of the pipe 76 is immersed within the test liquid. The pipe 76 is also used for the air conduit 70, and the upper end of the pipe 76 communicating with the air pipe 70. The lower portion of the pipe 76 is threadedly connected to the thread portion 21c of the joint 21. A circular cone shaped air guide member 28 is positioned in the casing 20. The lower portion of the joint 21 is connected to the casing 26 by the thread portion 22, and four windows 26a is apertured on the outer surface of the casing 26.

The test liquid may flow in and out through the window 26a, and may be contact with the sensing element 30. The lower portion of the casing 26 is secured and fitted to the electrode holder 27. The sensing element 30 is firmly secured by means of screwing the cap 29 in the electrode holder 27. On the contrary, the electrode holder 27 may be easily dismountable by taking apart the cap 29 from the electrode holder 27.

The circular slot 27a is formed into the electrode holder 27, as is stated above and as is best shown in FIG. 10, plural air outlet holes 27b are arranged circumferentially, and the air outlet holes 27 are communicated with the slot 27a in the inner portion of the electrode holder 27. The air conduit 70b connects the jointing metal 78a and 78b. And, further, as is best shown in FIG. 10 a refuse obstructing member such as a plate 160 is secured on the outer surface of the casing 26 by screws 23. Namely, the plate 160 is fixed to the casing 26 and electrode holder 27 by screws 23.

When the sensing device 20 equipped with the plate 160 is immersed into the test liquid, the sensing device 20 is positioned in the test liquid such that the plate 160 is positioned to the upper stream with respect to the jointing metals 78a and 78b.

In the above described construction, when the sensing element is placed in the test water, the test water flows in and out through the windows 26a from the casing 26 while contacting with the sensing element 30.

In the apparatus illustrated in FIG. 8, the valve 150 is closed during measurement of the dissolved oxygen content, and at the time when the sensing element 30 should be cleaned, a signal from the timer 90 is presented to the solenoid valve 150 and the air pump 80 through signal wires 40a and 40b, respectively. The solenoid valve 150 is opened by means of the signal from the timer 90, and, at the same time, the air pump 80 also becomes actuating condition. In this instance, the air is sent to the valve 150 by way of the air conduit 70a, and then the air sent to the valve 150 from the air pump 80 is further supplied to the slot 27a of the electrode holder 27 through the air conduit 70, the pipe 76, the tubular portion 21a and threaded hole 21 of the joint 21, the L-shaped and bent jointing metal 78a, the air conduit 70b and jointing metal 78b. The air supplied to the slot 27a is ejected to the inside of the casing 26 from the air outlet holes 27b.

At this time, the air ejected from the air outlet holes 27b becomes instantly many air bubbles 27, and the air bubbles float upward along to the sensing surface of the sensing element 30. In this case, the air bubbles act the disordered motion so that the exceeding turbulent flor is introduced in the vicinity of the surface of the sensing element 30. The lifted air bubbles are ultimately guided by the air bubble guiding member 28, and flows outward from the inside of the casing 26. At the same time, the test liquid is pumped up from the bottom portion of the casing 26 together with the air bubbles. In this instance, the sensing and electrode surface is cleaned continuously until a suspend signal is applied to the air compressor 80 and the valve 150.

In this case, a floating coarse refuse carrying with the test liquid conflicts with the float plate 160, and is carried down toward the vertical directions with respect to stream lines of the test liquid. Therefore, the coarse refuse will never clings to the casing 26, as a result the cleaning and measuring functions of the sensing device 20 will not be missed out.

In addition to this, the translational motion energy of the test liquid carrying down towards the directions as indicated an arrow 170 is converted into the vortex energy after the collision to the refuse obstructing member, and a part of the translational motion energy changes into the vortex energy generated in the downstream side of the plate 160. By this vortex energy, the test liquid may flow in and out in spite of the provision of the refuse obstructing member at the upper stream side of the sensing device 20. Accordingly, the motion of the flow of the test liquid becomes mainly eddy motion, and the translational motion is gradually reduced. Consequently, cleaning effects increase because the air bubbles are pumped up along the sensing element 30 without carrying down from the sensing device 20.

Figure 12:
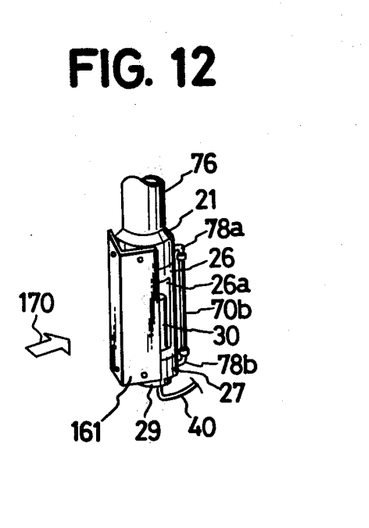
FIG. 12 is a schematic view of another form of FIG. 11.

FIG. 12 shows an another modifying form of the dissolved oxygen meter according to the third embodiment. In the dissolved oxygen meter of FIG. 12, employed is a bent plate 161 forming an obtuse angle against the stream direction of the test liquid, and it is evident that the dissolved oxygen meter 20 of FIG. 12 acts the same function as the dissolved oxygen meter 20 of FIG. 11.

As is stated above, as the sensing element 30 is cleaned by means of the natural rising of air bubbles, it may use an economical and small shaped sensing element because the sensing element does not so requires the mechanical strnegth. The time interval and the duty cycle to clean the sensing element may be selected in accordance with the rate of the contamination of sensing element. And, further, as there is no movable portion in the immersing portion of the dissolved oxygen meter of the present invention, malfunctions and abrasion may not almost be occured in the sensing device.

A small air pomp and a blower may be enough to use as an air source, because the air source is necessary to generate the air pressure such as usually 0.2 through 0.4 Kg/cm$^2$g in order to produce the air bubbles. It is, therefore, advantageous for the maintenance and the elimination of cost of the apparatus.

When the dissolved oxygen meter is used in a aeration tank of the treating station, it may use an air source of deaeration (where the air pressure is 0.5-0.6 Kg/cm$^2$g).

From the aforementioned description it can be seen that the following various advantages are obtained;

(1) The sensing element may be always maintained to clean and the accurate measurement can be accomplished, since the sensing device is cleaned by means of floating of air bubbles.

(2) Since the refuse obstructing member is used, the rough refuse will not cling to the sensing device, and a cleaning and a measuring performances are enhanced.

(3) Since the stream of the test liquid becomes vortex flows thanking to the refuse obstructing member, air bubbles will not be carried down even when the test liquid flows violently, the cleaning effect is extremely increased.

(4) Even when the refuse clings to the air generating hole and the casing it is easy to maintenance the apparatus due to the simple construction of the sensing device.

(5) The more effective advantage of the invention is fact that, since the turbulent flow of test liquid owing to the random motion is employed to clean the sensing element, the floc of sludge will not be destroyed and, as a result, the treatment of water can be performed adequately and effectively.

Figure 13:
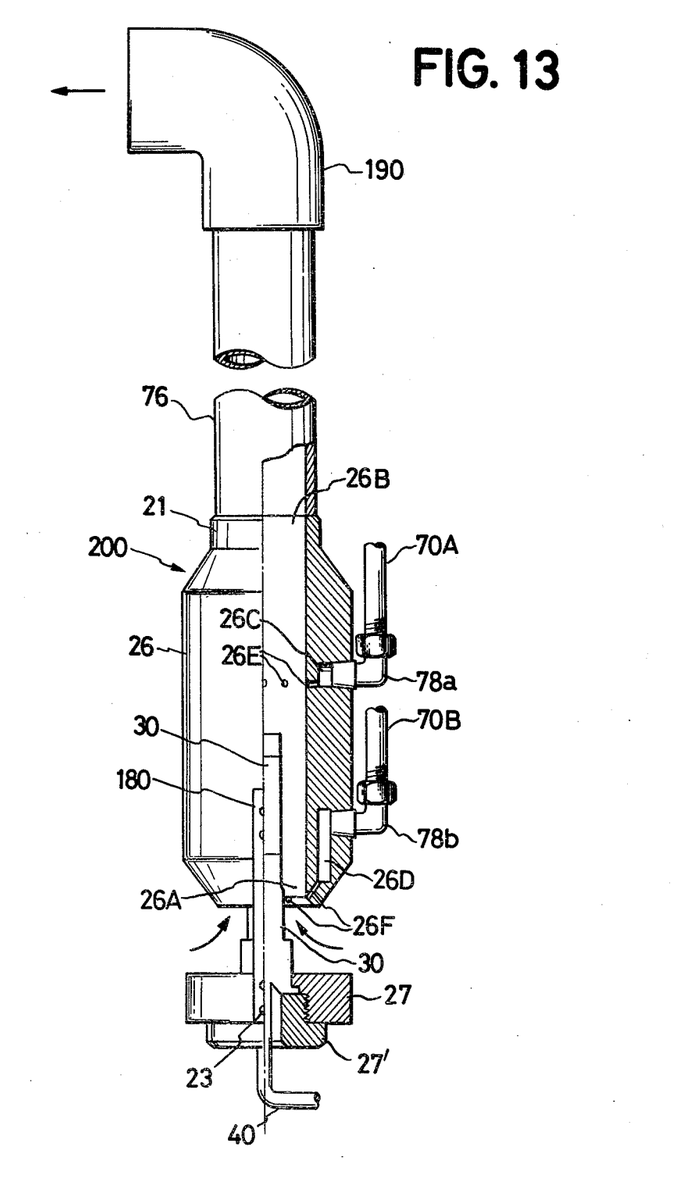
FIG. 13 is a partial sectional view of a sensing device of the third embodiment of the present invention.

FIGS. 13 through 19 show a fourth embodiment and an apparatus for facilitating the present invention, and referring particularly to FIG. 13, the sensing device 20 is best shown (in FIG. 3). The apparatus is composed of a test water moving means which includes an air-lift pump. As is best shown in FIG. 13, an air lift pump 200 mainly comprise a tubular casing 26 incorporating a sensing element 30, a conduit 76 jointly connected to the casing 26, an elbow 190 connected to the conduit 76.

The casing 26 is placed in the test liquid at the vertical position. The sensing element 30 is inserted in the casing 26, and holders 27 and 27' are dismountably secured at spaced-apart condition to the lower end portion of the sensing element 30, and a fixed member such as a bar 180 is secured between the holder 27 and the casing 26 by screws 23 or the like so as to be positioned at the center portion of the casing 26 through a circular gap. A lower open end 26A, therefore forms a sampling port.

The tubular pipe 76 is joined to an upper end by means of a screw or a bonding agent (not shown in the drawing), and an upper end of the pipe 76 is jointed to one end of a L-shaped elbow 190. A circular cavity 26C is provided on the upper end of the casing 26 and a circular cavity 26D is provided in the lower end portion of the casing 26. A plurality of air spraying ports 22E are opened in the upper internal wall surface of the casing 26 so as to communicate with the cavity 26C, and a plurality of air spraying ports 26F are opened in the lower end internal wall toward the lower open end of the casing 26. A first jointing metal tube 78a is communicated and jointed to the cavity 26C, and a second jointing metal tube 78b is connected and communicated with the cavity 26A.

One end of the first air pipe 70A is connected to the upper cavity 26C through the first jointing tube 78a, and the other end of the first air pipe 70A is usually connected to an air source such as an air pump through a conventional three-way solenoid valve (not shown in FIG. 13). And, further, one end of the second air pipe 70B is connected to the lower cavity 26D through the second jointing tube 78b, and the other end of the second air pipe 70B may be connected to the air source in the same manner as the first air pipe 70A. As a result, the air lift pump 200 is constructed by the casing 26, the air spraying port 26E, the first jointing tube 78a, the first air pipe 70A and the air source.

The operation of the sensing device 20 of FIG. 13 will now be described. The sensing device 20 (air lift pump 200) is generally immersed into the test liquid in the polluted liquid treating station so as to be immersed to air conduit 76, and during measurement, the air is supplied from the air source to the upper cavity 26C through the three way solenoid valve, the first air pipe 70A and the first jointing tube 78a. The air supplied to the cavity 26C is discharged through the air spraying ports 26E in the casing 26 as air bubbles to reduce the apparent specific gravity of the test liquid in the casing 26, so that the test water is drawn up from the lower opened portion to the elbow 190 in the direction as indicated by the arrows in FIG. 13. Then the drawn up water is discharged from the outlet of the elbow 190, due to the presence of air bubbles to be passed around the sensing element 30 at a predetermined flow rate. In this like manner, the correct measurement may be carried out, because a detected signal is sent to the system by way of the signal wire 40.

Furthermore, during the time interval of cleaning the sensing element 30, the air is supplied to the cavity 26D through the solenoid valve, the second air pipe 70B, and thereafter the air in the cavity 26D is ejected to the inside of the casing 26. The ejected air from the air spraying ports 26F are drawn up toward the upper direction while being contact with the sensing element 30 and motioning at random condition, so that the sensing element 30 is cleaned out by air bubbles.

In this case, during the measuring time, the test water filled up the water surface in the air pipe 70B extending to the water surface. When a signal to clean the sensing element 30 is presented, the filled water in the air pipe 70B is initially ejected from the air spraying holes 26F by way of the jointing member 78b, and the cavity 26D, until the water is discharged up from the air pipe 70B.

Therefore, the air pressure within the air pipe 70B becomes temporarily higher than that of the usual condition.

Accordingly, the air bubble ejecting force becomes extremely large and, as a result, the suspending refuse is removed from the sampling hole 26A by the large air bubble discharging force at the transient time when the ejecting matter is changed from the water to the air.

In addition, although an accurate measurement can be performed, because the test water flows upward within the casing 26 by means of the air-lift effect due to air bubbles generating from the air spraying holes 26F, the deviation of the desolved oxygen is, more or less, produced by the influence of the air bubble.

However, the deviation is approximately 1 percent, therefore, it may possible to accomplish the measurement and the cleaning at the same time, if the deviation is negligible, so that the route of the air pipe 70A is omissible.

Figure 14:
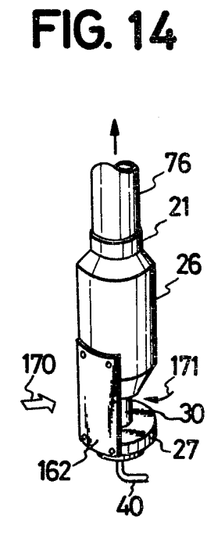
FIGS. 14 through 18 are various modifying form of the sensing device of FIG. 13.
Figure 15:
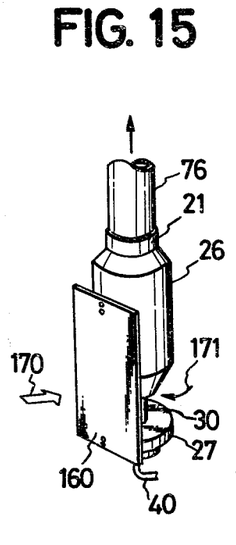
Figure 16:
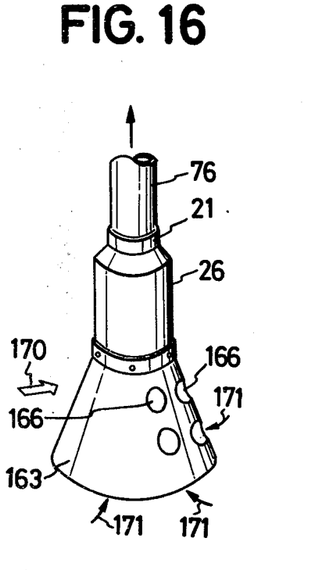

Additionally, according to the apparatus of the fourth embodiment, as is shown in FIGS. 14 through 16 refuse obstructing members are attached to the outer circumferential part of the lower open end portion 26A of the casing 26 in order to prevent the coarse insettling refuse from clinging and suspending to the lower open end 26A that is the sampling port.

In case of the sensing device 20 of FIG. 14, a semi-circular plate 162 is fastened to the casing 26 and the electrode holder 27 by screws, and in the sensing device 20, the flat plate 160 is fastened to the casing 26 and the electrode holder 27 in the same manner as that of FIG. 14. The sensing device of FIG. 16 equipes with a circular cone tube shaped skirt 163 as the refuse obstructing member, and a plurality of holes 166 is provided at the downstream side of the test liquid.

Figure 19:
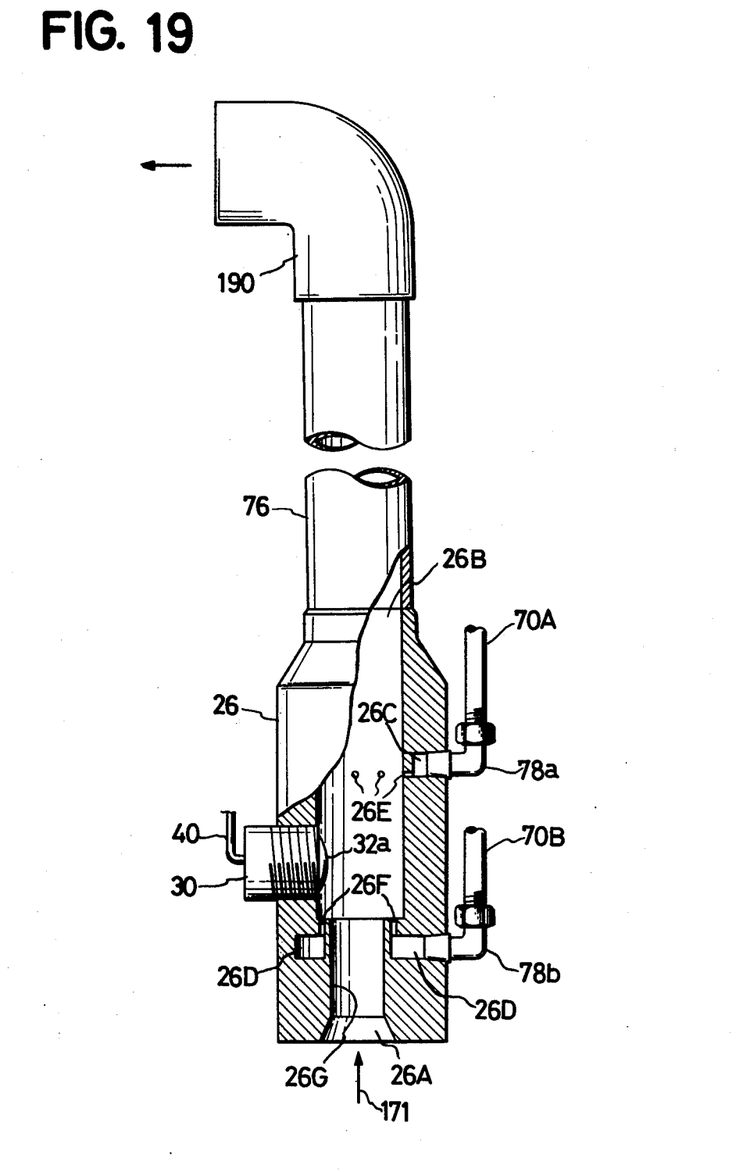
FIG. 19 is a partial sectional view of another form of sensing device according to the present invention.

Referring particularly to FIG. 19, illustrated is another modifying form of the structure of a sensing device 20 of the invention.

Figure 17:
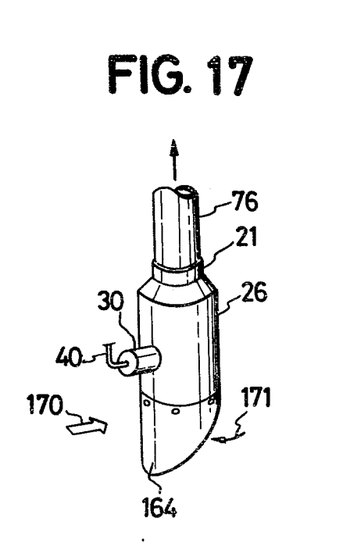
Figure 18:
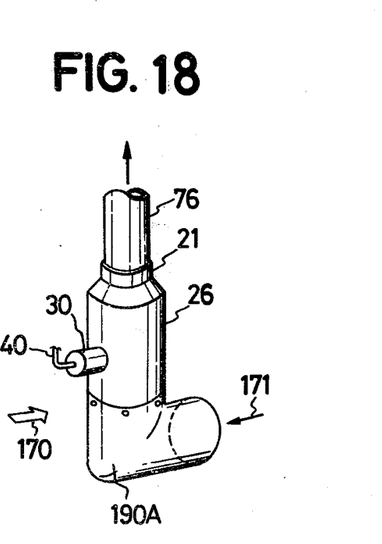

As is best shown in FIG. 19, a forward end face sensing type electrode is employed as a sensing element 30, and a sensing surface 32a is exposed within the casing 26 from the side wall thereof. The sensing surface 32a of the sensing element 30 is situated between the upper positioned air spraying holes 26E and the lower positioned air spraying holes 26F. An axial cylindrical hole 26G is provided in the lower end portion of the casing 26, and also communicates with the sampling port 26A at the internal side of axially opened air spraying holes 26F, so that a mixture of air bubbles and the liquid can be easily drawn up in the casing 26. In the sensing device of FIG. 19, the refuse obstructing member is mounted on the casing 26 as shown in FIGS. 17 and 18. Namely, in FIG. 17, fixed is on a tubular refuse obstructing member 164 in which the cylinder tube is cut diagonally as shown, and morefurther, in the case of FIG. 18, an elbow 190A is connected to the lower portion of the casing 26 so that the one open end of the elbow 190A is faced to the stream direction of the test liquid.

Although all the embodiments have been described only in connection dissolved oxygen meters, it should be understood that the present invention is not limited to the use for such meters but that it may be applicable to any other measuring instruments using electrode as a sensor such as PH meters, oxidation-reduction meters and the like effecting electromechanical measurements and turbidity meters and suspended soiled meters for effecting optical measurements.

From the aformentioned description, according to the present invention, since an apparatus includes an air bubble generating means positioned substantially in the vicinity of a sensing element for obtaining the measuring information, and since an excessive turbulent flow is generated in the vicinity of a sensing element by the substantially disordered motion due to the floating power of air bubbles by said air bubble generating means, it can be seen that an economical apparatus may be obtained because an economical and low pressure gas source can be used for cleaning a sensing element.

It can also be seen that the lowering of the sensitivity of the sensing element due to the adherence of contaminants is thus almost completely avoided to thereby lengthen the time interval between maintenance services as well as permitting accurate measurements for a long period of time.

While the invention has been particularly described with reference to preferred embodiment, changes and modification may be easily possible to those skilled in the art. But it is intended to cover all the changes and modifications which do not constitute departures from the sprit and scope of the invention.

What is claimed is:

1. An apparatus for determining amounts of matter dissolved and suspended in a test liquid, which amounts serve to indicate characteristics of the test liquid for cleaning a sensing surface of a sensing element (30) and for preventing the decrement of the test liquid, the apparatus comprising:

(a) means for sensing matter dissolved in the test liquid, including a sensing device (20) which includes a tubular casing (26), provided with at least one opening portion (26a, 26A, 26B) allowing the test liquid to flow in and out, said sensing surface of the sensing element (30) being disposed in said casing 26 at the liquid to detect amounts of matter, (b) air-bubble means in the vicinity of said sensing element for producing turbulent flow responsive to the substantially disordered motion including a normal line direction of said sensing surface and the buoyance of air bubbles in the vicinity of said sensing surface, said generating means having an air spraying member (27, 26D) integrated with a lower portion of said casing and an air spraying hole (27b, 26F) disposed on a lower side of said sensing element, (c) means for supplying air to the interior of said air-bubble generating means, including an air conduit (70, 70B) communicating at one end with the interior of said air spraying member, (d) a tubular joining member (21) having a first end portion connected in substantially liquid-tight relationship to said casing, (e) and a pipe member (76) connected to a second end portion of said tubular joining member.

2. The apparatus as defined in claim 1, wherein: said casing (26) is provided with at least one window-through which the test liquid can flow in and out, and an air-bubble guiding member (28) for aiding the flow of the air bubbles.

3. The apparatus as defined in claim 1, wherein: said casing (26) is provided with said sensing element (30) and at least one window (26a) provided substantially on the circumferential side surface thereof, through which the test liquid can flow; a second sensing element (30) incorporated into said tubular casing, and an air generating member (27) having an electrode support member (27) for supporting said sensing element (30) and being interconnected to an open end portion of said tubular casing to form said air-bubble generating means, a circular slot (27a) formed within said support member and a plurality of small axially disposed holes (27b) being circumferentially arranged in said support member, to communicate with said slot.

4. The apparatus as defined in claim 3, wherein: a pipe member (76) is provided having one end portion connected in a substantially liquid-tight relationship to a first air conduit (74), a tubular joining member (21) having a first end formed with a hollow circular part, and a second end with a circular, cone-shaped air-bubble guiding member (28), said circular part being interconnected to a second end portion of said pipe member, said record end of the joining member being connected and joined to said tubular casing (26) so that said air-bubble guiding member is located in said casing, and further said circular part is joined and communicates with said slot (27a) of said support member (27).

5. The apparatus as defined in claim 1, wherein: a refuse obstructing member (160) mounted on said casing (26) being disposed to prevent rough refuse, carried from the upper stream of the test liquid, from clinging to said sensing element (30).

6. The apparatus as defined in claim 1, wherein: means (200) are provided for moving the test liquid into contact with said sensing element (30), parallel to and relative to the latter.

7. The apparatus as defined in claim 6, wherein: a refuse obstructing member (160) is mounted on said casing (26) so as to prevent rough refuse, carried from the upper stream of the test liquid, from clinging to said casing.

8. The apparatus as defined in claim 6, wherein: said casing (26) is tubular and accommodates said sensing element (30), said air-bubble generating means including a first, circular cavity (26D) provided on one open end portion of said casing, a plurality of second air spraying ports (26F) communicating with said first cavity for producing air bubbles to clean said sensing element by means of the turbulent flow generated in the vicinity of said sensing surface, test-liquid sensing means including an air-lift pump (200) having a second circular cavity (26C) provided on said casing above said sensing element, a plurality of first air spraying ports opening in a radial direction of said casing so as to communicate with said second cavity, air supplying means defined by a first air conduit (70A) communicating with said second cavity by way of a first conduit member (78a) and a second air conduit (70B) communicating with said first cavity through a second conduit member (70b).

9. The apparatus as defined in claim 8, wherein: an electrode support member (27) is provided for supporting said sensing element (30), mounted on said casing (26) in a spaced apart relationship from a lower open end portion of said casing, a signal wire (40) connected electrically to said sensing element, and a pipe (76) connected to an upper end portion of said casing so as to communicate with the latter.

10. An apparatus as defined in claim 1, wherein: said sensing element (30) is a forward end face sensing type electrode having a surface (32a) which is exposed within the casing (26) from the side wall thereof, and said air-bubble generating means includes a first circular cavity (26D) provided on one open end portion of said casing, a plurality of second air spraying parts (26F) which are axially and circumferentially provided on said casing so as to be positioned in the lower side of said sensing surface (32a) to thereby communicate with said first cavity (26D).

11. The apparatus as defined in claim 1, wherein: said casing (26) is provided with said sensing element (30) and at least one window (26a) substantially at the circumferential side surface thereof, through which the test liquid can flow; a sensing element (30) incorporated into said tubular casing, and an air generating member (27) having an electrode support member (27) for supporting said sensing element (30) being interconnected to an open end portion of said tubular casing to form said air-bubble generating means, a circular slot (27a) formed within said support member and a plurality of small axially disposed holes (27b) being circumferentially arranged in said support member, to communicate with said slot.

* * * * *